United States Patent
Miyamoto (10) Patent No.: US 11,915,726 B2
(45) Date of Patent: *Feb. 27, 2024

(54) RECORDING DEVICE, READOUT DEVICE, RECORDING METHOD, RECORDING PROGRAM, READOUT METHOD, READOUT PROGRAM, AND MAGNETIC TAPE CAPABLE OF SHORTENING THE READING OF DATA RECORDED ON A RECORDING MEDIUM

(71) Applicant: FUJIFILM CORPORATION, Tokyo (JP)

(72) Inventor: Kentaro Miyamoto, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 380 days.

This patent is subject to a terminal disclaimer.

(21) Appl. No.: 17/210,507

(22) Filed: Mar. 24, 2021

(65) Prior Publication Data

US 2021/0210120 A1    Jul. 8, 2021

Related U.S. Application Data

(63) Continuation of application No. PCT/JP2019/032849, filed on Aug. 22, 2019.

(30) Foreign Application Priority Data

Sep. 26, 2018    (JP) .................................. 2018-180774

(51) Int. Cl.
*G11B 27/10*    (2006.01)
*G06F 3/06*    (2006.01)
(Continued)

(52) U.S. Cl.
CPC .............. *G11B 27/107* (2013.01); *G06F 3/06* (2013.01); *G11B 20/10* (2013.01); *G11B 27/10* (2013.01);
(Continued)

(58) Field of Classification Search
None
See application file for complete search history.

(56) References Cited

U.S. PATENT DOCUMENTS

| 5,870,523 A | 2/1999 | Kikuchi et al. |
| 5,889,746 A | 3/1999 | Moriyama et al. |

(Continued)

FOREIGN PATENT DOCUMENTS

| CN | 1134583 A | 10/1996 |
| CN | 1260567 A | 7/2000 |

(Continued)

OTHER PUBLICATIONS

English language translation of the following: Office action dated Dec. 3, 2021 from the SIPO in a Chinese patent application No. 201980063173.9 corresponding to the instant patent application. This office action translation is submitted now in order to supplement the understanding of the cited references which are being disclosed in the instant Information Disclosure Statement.

(Continued)

*Primary Examiner* — Craig A. Renner
(74) *Attorney, Agent, or Firm* — SOLARIS Intellectual Property Group, PLLC (57) ABSTRACT

A recording device that generates a hierarchy of groups for classifying each of a plurality of data to be recorded from information on each of the data, and performs a control of recording, for each group of a highest hierarchy, the plurality of data included in the group of the highest hierarchy on a (Continued)

recording medium in a recording order corresponding to an order from the top to the bottom of the hierarchy.

7 Claims, 10 Drawing Sheets

(51) Int. Cl.
*G11B 20/10* (2006.01)
*G11B 27/32* (2006.01)
*G16H 10/60* (2018.01)
*G16H 30/00* (2018.01)
*G11B 27/00* (2006.01)

(52) U.S. Cl.
CPC ........... *G11B 27/328* (2013.01); *G16H 10/60* (2018.01); *G16H 30/00* (2018.01); *G11B 27/002* (2013.01); *G11B 2220/41* (2013.01); *G11B 2220/90* (2013.01)

(56) References Cited

U.S. PATENT DOCUMENTS

| | | | |
|---|---|---|---|
| 6,345,017 | B1 | 2/2002 | Inoue |
| 11,373,674 | B2 * | 6/2022 | Ozawa et al. ..... G11B 5/00813 |
| 2005/0108466 | A1 | 5/2005 | Takashima et al. |
| 2005/0254410 | A1 | 11/2005 | Kibe et al. |
| 2007/0268971 | A1 | 11/2007 | Kato |
| 2012/0029939 | A1 | 2/2012 | Danielson et al. |
| 2014/0268399 | A1 | 9/2014 | Katagiri et al. |

FOREIGN PATENT DOCUMENTS

| | | |
|---|---|---|
| CN | 1617252 A | 5/2005 |
| CN | 102611898 A | 7/2012 |
| CN | 103238165 A | 8/2013 |
| GB | 807437 A | 1/1959 |
| JP | H05-282796 A | 10/1993 |
| JP | H09-265765 A | 10/1997 |
| JP | H10-177642 A | 6/1998 |
| JP | 2006-004588 A | 1/2006 |
| JP | 2007-313219 A | 12/2007 |
| JP | 2013-222489 A | 10/2013 |

OTHER PUBLICATIONS

English language translation of the following: Office action dated Apr. 28, 2022 from the SIPO in a Chinese patent application No. 201980063173.9 corresponding to the instant patent application. This office action translation is submitted now in order to supplement the understanding of the cited references which are being disclosed in the instant Information Disclosure Statement.
International Search Report issued in International Application No. PCT/JP2019/032849 dated Nov. 12, 2019.
Written Opinion of the ISA issued in International Application No. PCT/JP2019/032849 dated Nov. 12, 2019.
Extended European Search Report dated Jul. 1, 2021, issued in corresponding EP Patent Application No. 19864139.1.
Coughlan, Michael, "Sorting and Merging files", Apr. 30, 1999, pp. 1-20, XP055816874, Retrieved from the Internet:URL:http ://www.csis.ul.i e/cobol/course/SortMerge.htm [retrieved on Jun. 22, 2021] * the whole document*.
Anonymous: "File Organization in Data Structure", Dec. 31, 2017, pp. 1-4, XP055816871, Retrieved from the Internet :URL:https://www.tutorialride.com/data-structures/file-organization-in-data-structure.htm [retrieved on Jun. 22, 2021] * p. 2*.
Anonymous: "Sequential File Design", Jan. 6, 1999, pp. 1-3, XP055817165, Retrieved from the Internet:URL:https://www.slawinski.ca/courses/ IP10/Unit9/part7.htm [retrieved on Jun. 23, 2021] p. 2.
Anonymous: "Copying Directories Between File System (cpio Command)-Oracle Solaris Administration: Devices and File Systems", Jan. 1, 2012, pp. 1-3 XP055817082, Retrieved from the Internet :URL:https://docs.oracle.com/cd/ E23824 01/ html /821-1459/ bkupsavefiles-21.html #[retreived on Jun. 23, 2021] * p. 1 *.
Copying directories between file systems using cpio commend, Solaris system management vol. 1, Dec. 2010, retrieved from <https://docs.oracle.com/cd/E19455-01/806-2717/6jbtqlek3/index.html>.
English language translation of the following: Office action dated Jun. 7, 2022 from the JPO in a Japanese patent application No. 2020-548175 corresponding to the instant patent application. This office action translation is submitted now in order to supplement the understanding of the cited reference which is being disclosed in the instant Information Disclosure Statement.

* cited by examiner

| PATIENT NAME (PATIENT A) | | | | | PATIENT NAME (PATIENT B) |
|---|---|---|---|---|---|
| DIAGNOSIS DATE (7/1/2018) | | | DIAGNOSIS DATE (8/1/2018) | | ⋮ |
| MEDICAL IMAGE | | DIAGNOSTIC INFORMATION | MEDICAL IMAGE | | DIAGNOSTIC INFORMATION | ⋮ |
| CT | MRI | | CT | MRI | | ⋮ |
| | | | | | | ⋮ |

↑ OBJECT

| DIAGNOSIS DATE (7/1/2018) | | | | | | DIAGNOSIS DATE (8/1/2018) | |
|---|---|---|---|---|---|---|---|
| PATIENT NAME (PATIENT A) | | | PATIENT NAME (PATIENT B) | | | ⋮ | ⋮ |
| MEDICAL IMAGE | | DIAGNOSTIC INFORMATION | MEDICAL IMAGE | | DIAGNOSTIC INFORMATION | ⋮ | ⋮ |
| CT | MRI | | CT | MRI | | ⋮ | ⋮ |
| ↑ OBJECT | | | | | | | |

RECORDING DEVICE, READOUT DEVICE, RECORDING METHOD, RECORDING PROGRAM, READOUT METHOD, READOUT PROGRAM, AND MAGNETIC TAPE CAPABLE OF SHORTENING THE READING OF DATA RECORDED ON A RECORDING MEDIUM

CROSS-REFERENCE TO RELATED APPLICATION

This application is a continuation of International Application No. PCT/JP2019/032849, filed on Aug. 22, 2019, which claims priority to Japanese Patent Application No. 2018-180774, filed on Sep. 26, 2018. The entire disclosures of both of the above-referenced applications are hereby incorporated by reference into the present application.

BACKGROUND

Technical Field of the Invention

The present disclosure relates to a recording device, a readout device, a recording method, a recording medium, a readout method, and a magnetic tape.

Related Art

A technology for recording image data representing a medical image and information on image data such as a patient name on a recording medium is disclosed (refer to JP2013-222489A).

In addition, a data storage method is disclosed in which a file and a directory in which file information is stored are stored in a physically continuous region of a compact disc read only memory (CD-ROM) (refer to JP1993-282796A (JP-H05-282796A)).

In a case where a plurality of data are recorded on a recording medium, by recording the plurality of data on the recording medium in a recording order in consideration of the possibility that the data are read together after recording, the reading time at the time of reading the data can be shortened in some cases.

However, in the technology disclosed in JP2013-222489A and JP1993-282796A (JP-H05-282796A), such an order in which data is recorded on the recording medium is not considered.

SUMMARY

A recording device of the present disclosure includes: a memory; and a processor that is coupled to the memory, the processor being configured to: generate a hierarchy of groups for classifying each of a plurality of data to be recorded from information on each of the data, and perform a control of recording, for each group of the highest hierarchy, the plurality of data included in the group of the highest hierarchy on a recording medium in a recording order corresponding to an order from the top to the bottom of the hierarchy.

DETAILED DESCRIPTION

Hereinafter, an example of an aspect for carrying out the technology of the present disclosure will be described in detail with reference to the drawings.

First Embodiment

Figure 1:
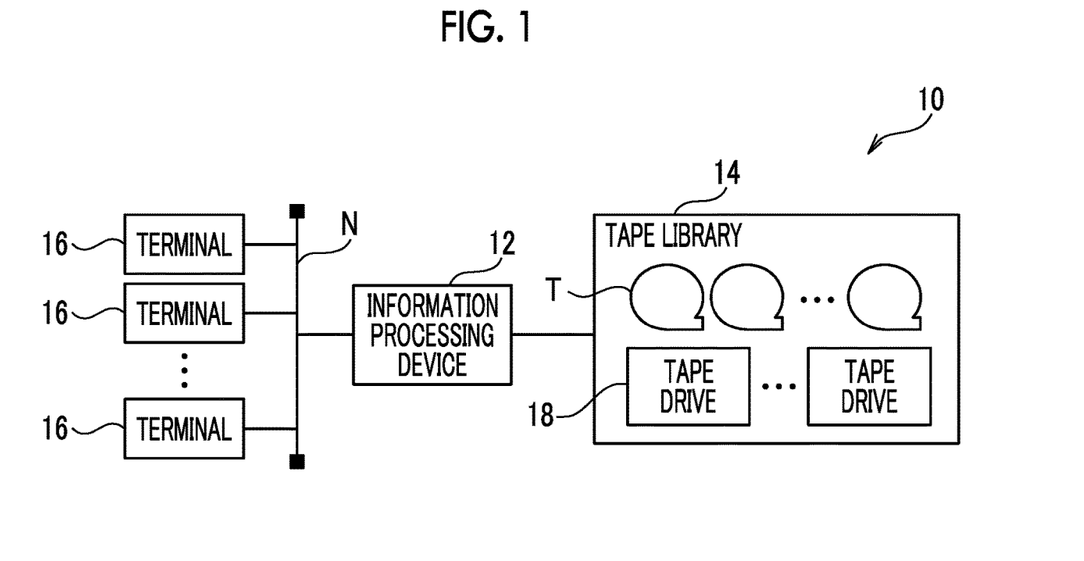
FIG. 1 is a block diagram showing an example of a configuration of a recording/readout system according to each embodiment.

First, a configuration of a recording/readout system 10 according to the present embodiment will be described with reference to FIG. 1. As shown in FIG. 1, the recording/readout system 10 includes an information processing device 12 and a tape library 14. The tape library 14 is connected to the information processing device 12. In addition, the information processing device 12 and a plurality of terminals 16 are connected to a network N and can communicate via the network N.

The tape library 14 comprises a plurality of slots and a plurality of tape drives 18, and a magnetic tape T as an example of a recording medium is stored in each slot. As an example of the magnetic tape T, a linear tape-open (LTO) tape can be included.

In a case where the information processing device 12 writes or reads data on the magnetic tape T, the magnetic tape T to be written or read is loaded from the slot into the predetermined tape drive 18. In a case where the information processing device 12 completes the writing or reading of the magnetic tape T loaded into the tape drive 18, the magnetic tape T is unloaded from the tape drive 18 to the originally stored slot.

In the present embodiment, as a unit for handling data to be recorded on the magnetic tape T, an example of an aspect in which an object including data to be stored by a user such as document data and image data and metadata, as an example of information, related to the data is applied will be described. A storage system that handles this object is called an object storage system. In addition, in the present embodiment, an aspect example in which medical data depending on a predetermined standard such as a digital imaging and communications in medicine (DICOM) is applied as data to be recorded on the magnetic tape T will be described.

Figure 2:
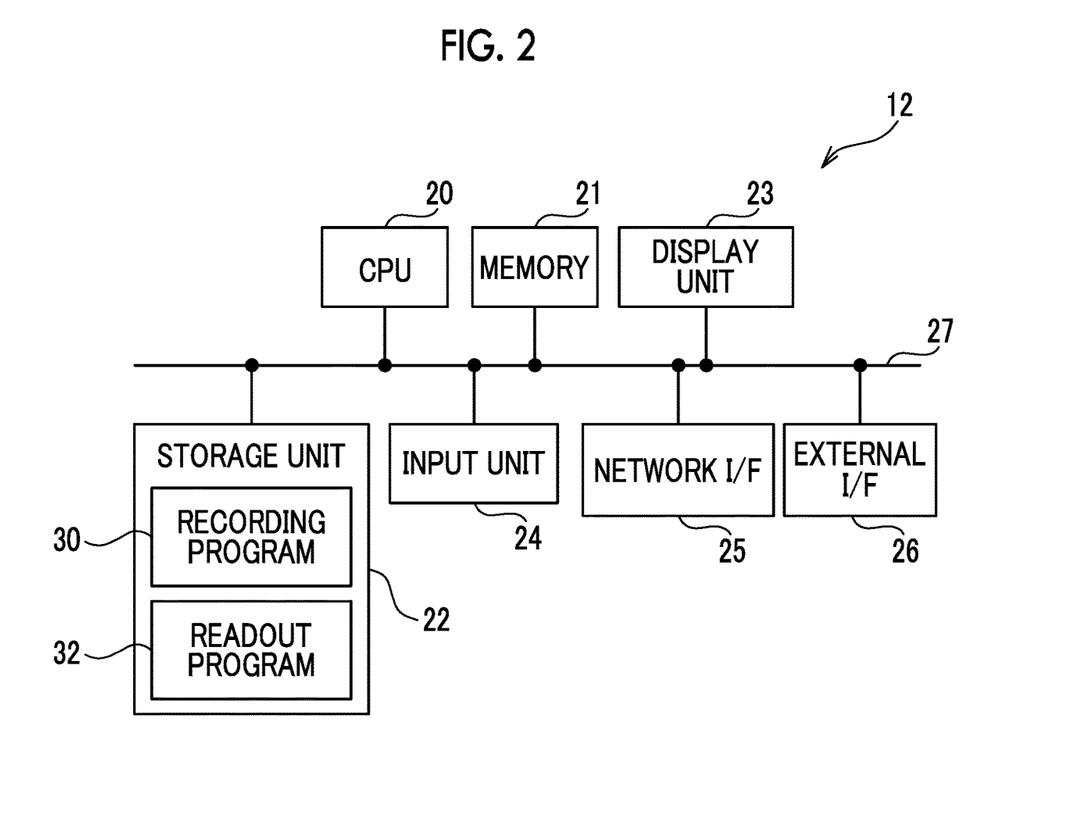
FIG. 2 is a block diagram showing an example of a hardware configuration of an information processing device according to each embodiment.

Next, a hardware configuration of the information processing device 12 according to the present embodiment will be described with reference to FIG. 2. As exemplified in FIG. 2, the information processing device 12 includes a central processing unit (CPU) 20, a memory 21 as a temporary storage region, and a nonvolatile storage unit 22. In addition, the information processing device 12 includes a display unit 23 such as a liquid crystal display, an input unit 24 such as a keyboard and a mouse, a network interface (I/F) 25 connected to the network N, and an external I/F 26 connected to the tape library 14. The CPU 20, the memory 21, the storage unit 22, the display unit 23, the input unit 24, the network I/F 25, and the external I/F 26 are connected to a bus 27.

The storage unit 22 is realized by a hard disk drive (HDD), a solid state drive (SSD), a flash memory, and the like. A recording program 30 and a readout program 32 are stored in the storage unit 22 as a storage medium. The CPU 20 reads the recording program 30 from the storage unit 22, expands it in the memory 21, and loads and executes the expanded recording program 30. In addition, the CPU 20 reads the readout program 32 from the storage unit 22, expands it in the memory 21, and loads and executes the expanded readout program 32. It should be noted that as an example of the information processing device 12, a server computer or the like can be included. Further, the information processing device 12 is an example of a recording device that records an object on the magnetic tape T. Furthermore, the information processing device 12 is also an example of a readout device that reads the object recorded on the magnetic tape T.

Figure 3:
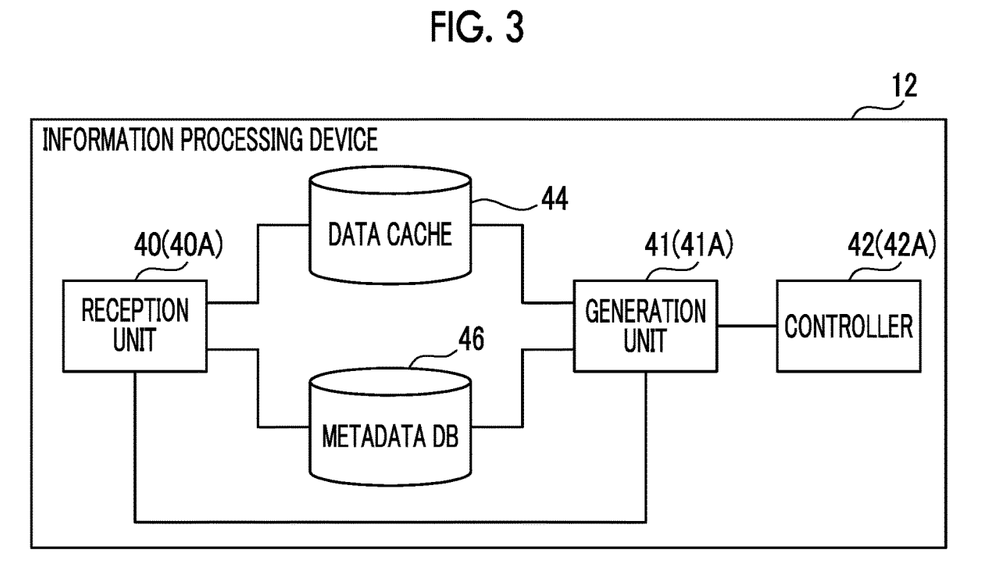
FIG. 3 is a block diagram showing an example of a functional configuration in a case of recording an object of an information processing device according to each embodiment.

Next, a functional configuration in a case where an object is recorded on the magnetic tape T of the information processing device 12 according to the present embodiment will be described with reference to FIG. 3. As shown in FIG. 3, the information processing device 12 includes a reception unit 40, a generation unit 41, and a controller 42. By executing the recording program 30, the CPU 20 functions as the reception unit 40, the generation unit 41, and the controller 42. In addition, in a predetermined storage region of the storage unit 22, there are a data cache 44 for storing an object to be described later and a metadata database (DB) 46 for storing metadata to be described later. Further, the data cache 44 and metadata DB 46 are prepared for each magnetic tape T.

The reception unit 40 receives, via the network I/F 25, data transmitted from the terminal 16 and metadata related to the data by using an application programming interface (API) for handling an object. Then, the reception unit 40 stores the received data in the data cache 44 and stores the metadata in the metadata DB 46. The metadata transmitted from the terminal 16 includes identification information such as a data name of corresponding data, a size of data, and attribute information indicating a data attribute such as a time stamp.

In a case where the corresponding data is a medical image, the attribute information included in the metadata according to the present embodiment includes a type of imaging device used for imaging the medical image (referred to as a modality). Examples of types of imaging device used for imaging medical images include a computed tomography (CT), a magnetic resonance imaging (MRI), and a positron emission tomography (PET). In addition, the attribute information included in the metadata includes a patient name for identifying which patient the corresponding data is related to, a diagnosis date of the corresponding data, and information on a diagnosis result described in a medical record (hereinafter referred to as "diagnostic information"). These attribute information contained in the metadata is included in the metadata with each attribute name tagged.

More specifically, for example, the metadata includes a tag "patient name" and information "patient A" corresponding to the tag.

Figure 4:
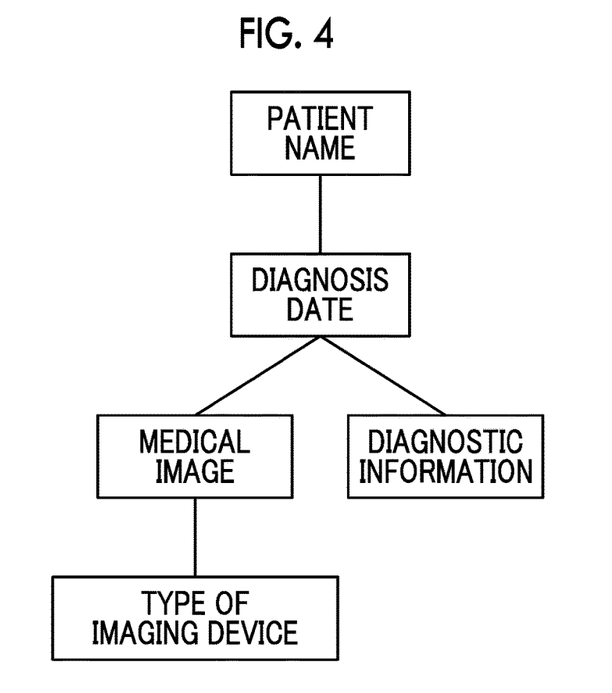
FIG. 4 is a diagram showing an example of hierarchical orders of a hierarchy according to each embodiment.

The reception unit 40 also receives information representing hierarchical orders of a hierarchy of a unit of the group for classifying each object, which is input by a user via the input unit 24. FIG. 4 shows an example of the hierarchical orders of the hierarchy. FIG. 4 shows an example in which "patient name", "diagnosis date", "medical image", "diagnostic information", and "type of imaging device" are designated as the group units. In addition, FIG. 4 shows an example in which "patient name" is the highest hierarchy, the lower hierarchy of "patient name" is "diagnosis date", the lower hierarchy of "diagnosis date" is "medical image" and "diagnostic information", and the lower hierarchy of "medical image" is "types of imaging device". It should be noted that the hierarchical orders of the hierarchy shown in FIG. 4 is an example, and is not limited to this example.

Figure 5:
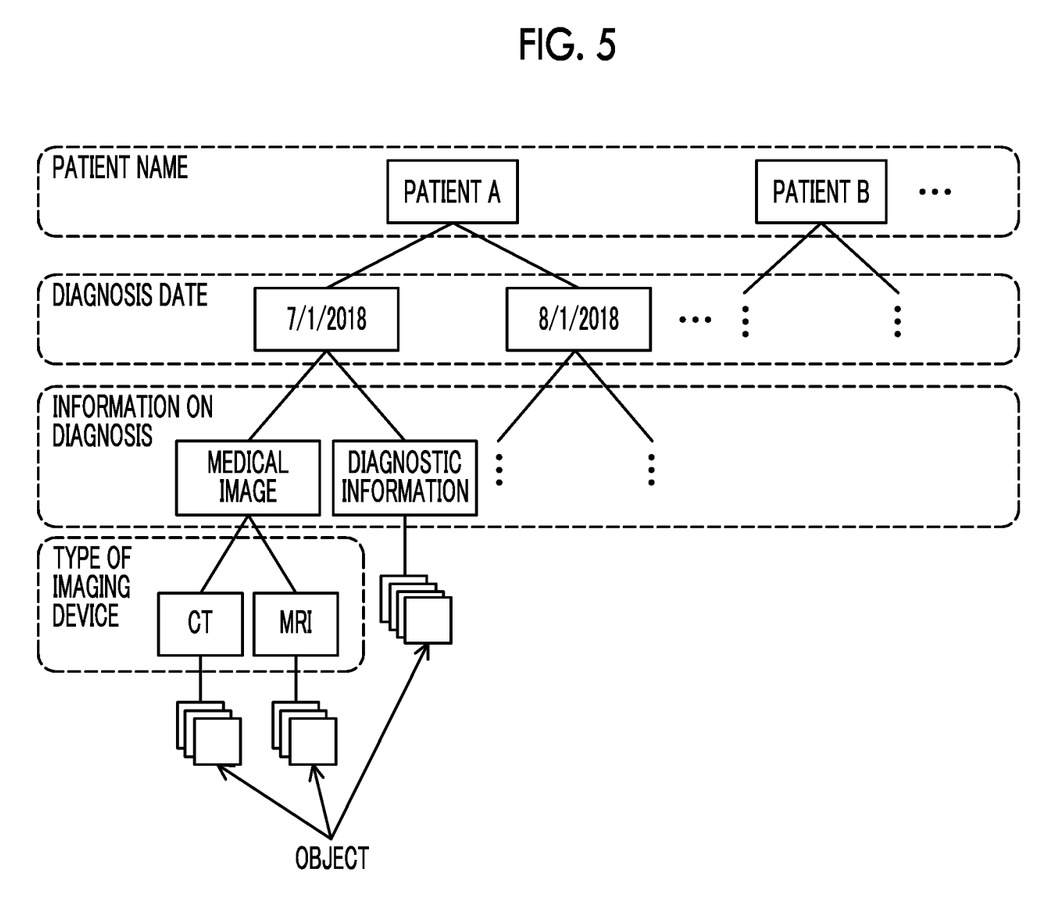
FIG. 5 is a diagram showing an example of hierarchies of groups according to each embodiment.

The generation unit 41 generates a hierarchy of groups for classifying each object from metadata of each of a plurality of objects to be recorded according to the information representing the hierarchical orders received by the reception unit 40. Specifically, the generation unit 41 generates a hierarchy of groups depending on the information representing the hierarchical orders from a tag of metadata included in each object and information corresponding to the tag. FIG. 5 shows an example of the hierarchy generated by the generation unit 41 according to the information shown in FIG. 4.

As shown in FIG. 5, an object group is grouped for the patient name which is the highest hierarchy, and further, the object group is grouped for the diagnosis date which is the lower hierarchy of the patient name. In addition, in the object group, an object group is grouped for each medical image and each diagnostic information which are lower hierarchy in the hierarchy of the diagnosis date, and further, the object group is grouped for each type of imaging device which is lower hierarchy in the medical image.

For objects included in the lowest hierarchical group (in the example of FIG. 5, "CT", "MRI", and "diagnostic information") shown in FIG. 5, all the traced groups in a case of traversing the hierarchy from the highest group to the lowest group are included in the metadata. Specifically, for example, objects included in "CT" shown in the lower left of FIG. 5 represent that "patient A" is included in the metadata as the patient name, "Jul. 1, 2018" is included as the diagnosis date, "medical image" is included as the type of data, and "CT" is included as the type of imaging device.

The controller 42 controls the tape library 14 and loads the magnetic tape T, on which an object is to be recorded, into a predetermined tape drive 18. In addition, the controller 42 performs a control of recording each object including the data stored in the data cache 44 and the corresponding metadata stored in the metadata DB 46 on the magnetic tape T in the following recording order. That is, in this case, the controller 42 performs a control of recording a plurality of objects included in the group of the highest hierarchy on the magnetic tape T in a recording order corresponding to an order from the top to the bottom of the hierarchy for each group of the highest hierarchy generated by the generation unit 41.

Figure 6:
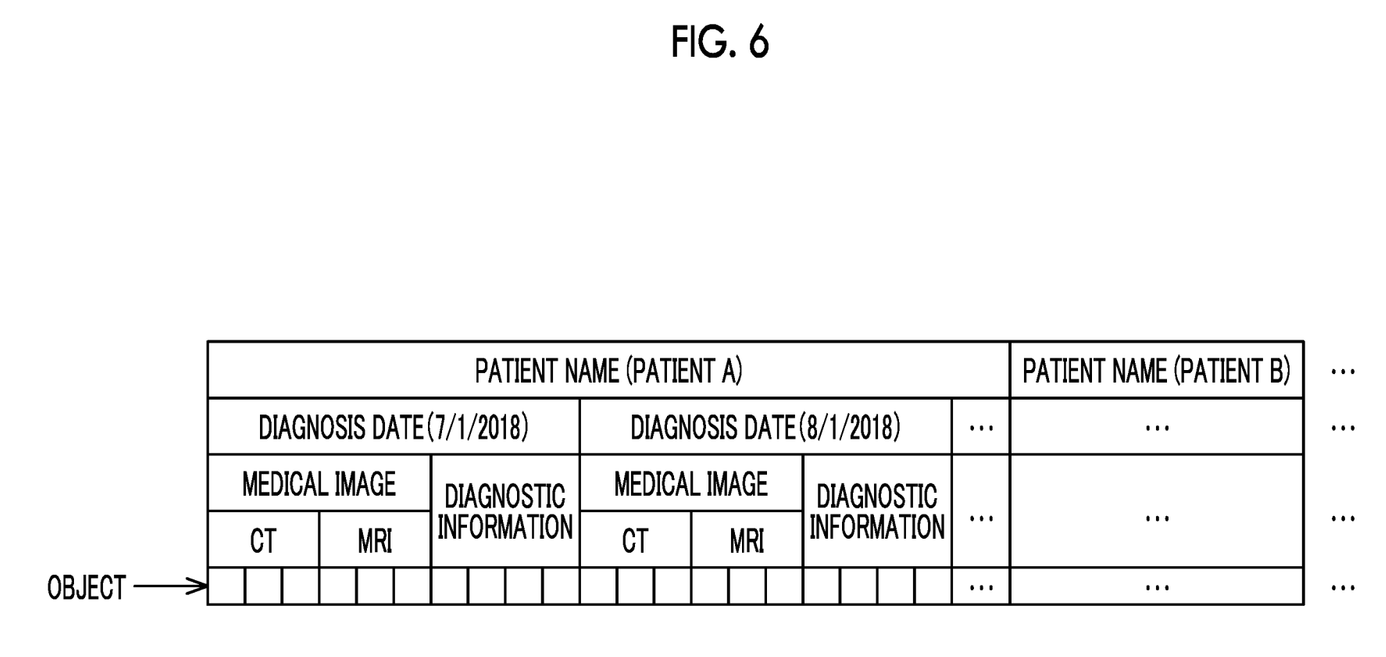
FIG. 6 is a diagram showing an example of a recording order of objects according to each embodiment.

An example of the detailed recording order of the object group shown in FIG. 5 will be described with reference to FIG. 6. As shown in FIG. 6, in the present embodiment, under the control of the controller 42, the objects to be recorded are arranged in an order of the patient name (in the example of FIG. 6, an order of "patient A" and "patient B") which is the highest hierarchy. In addition, the objects of the patients indicated by each patient name are arranged in the order of the diagnosis date (in the example of FIG. 6, an order of "Jul. 1, 2018" and "Aug. 1, 2018"), which is lower hierarchy in the patient name. In addition, the objects for each diagnosis date are arranged in an order of medical images and diagnostic information, which is lower hierarchy in the diagnosis date. Further, the objects of each medical image are arranged in an order of the types of imaging devices (in the example of FIG. 6, an order of "CT" and "MRI"), which is the lower hierarchy in the medical image.

Then, the controller 42 performs a control of recording a plurality of objects on the magnetic tape T with one recording instruction in the order arranged as described above. More specifically, the controller 42 outputs the recording instruction to the magnetic tape T to the controller comprised in the tape drive 18, and also outputs the recording instruction to the controller comprised in the tape drive 18 in an order in which each object is arranged as described above. The controller comprised in the tape drive 18 continuously records objects on the magnetic tape T according to the order input from the controller 42. That is, in the example of FIG. 6, the objects are recorded on the magnetic tape T in an order from the left side to the right side of FIG. 6.

The controller 42 performs a control of recording the hierarchy of the group generated by the generation unit 41 in a recording region (for example, a head portion of the magnetic tape T) in which management information of the magnetic tape T is recorded. It should be noted that the controller 42 may store the hierarchy of the group generated by the generation unit 41 in the storage unit 22 in association with the identification information of the magnetic tape T. Further, the controller 42 also performs a control of recording a recording position of a head object of each group in the recording region for recording the management information as a recording position on the magnetic tape T of each group.

It should be noted that the recording order of the groups in the parallel hierarchy is not particularly limited. The recording order of the groups in the parallel hierarchy may be random, the order of the group identification information, or may be designated by a user. Specifically, for example, FIG. 6 shows an example in which objects are recorded in an order of CT and MRI for CT and MRI which are the lower hierarchy in the medical image, but the objects may be recorded in an order of MRI and CT.

Figure 7:
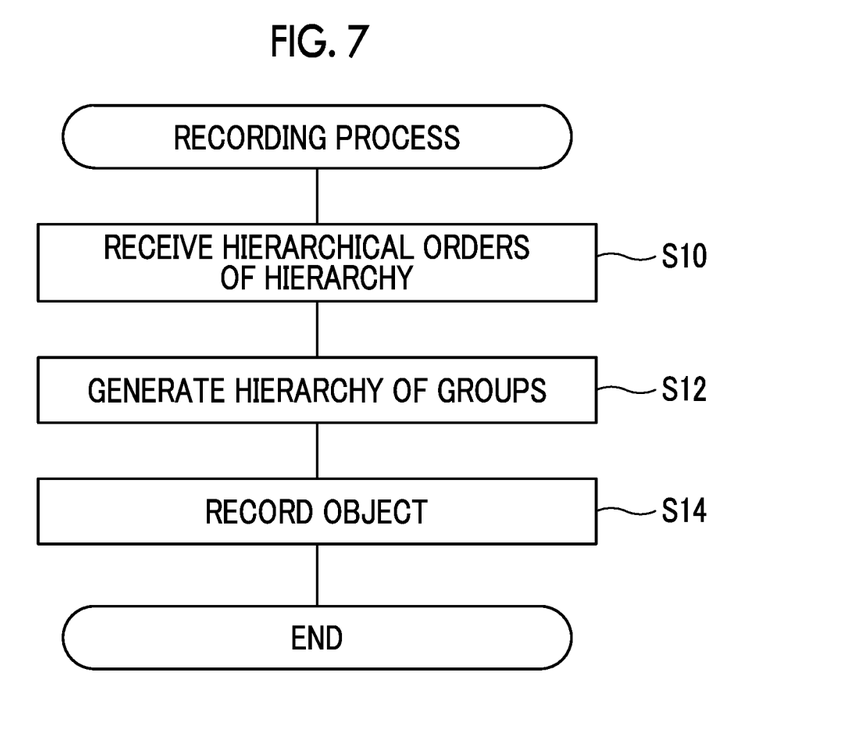
FIG. 7 is a flowchart showing an example of a recording process according to the first embodiment.

Next, an operation in a case where an object is recorded on the magnetic tape T of the information processing device 12 according to the present embodiment will be described with reference to FIG. 7. In a case where the CPU 20 executes the recording program 30, the recording process shown in FIG. 7 is executed. The recording process shown in FIG. 7 is executed, for example, in a case where the information representing the hierarchical orders of the hierarchy described above is input by a user via the input unit 24, and the recording instruction of the object is input. It should be noted that, for example, in a case where the information representing the hierarchical orders of the hierarchy is preset by the user and the total size of the data stored in the data cache 44 is equal to or larger than a threshold value, the recording process shown in FIG. 7 may be executed.

In step S10 of FIG. 7, as described above, the reception unit 40 receives the information representing the hierarchical orders of the hierarchy of the unit of the group for classifying each object. In step S12, as described above, the generation unit 41 generates a hierarchy of groups for classifying each object from the metadata of each of the plurality of objects to be recorded according to the information representing the hierarchical orders received by the process in step S10.

In step S14, as described above, the controller 42 performs a control of recording a plurality of objects included in the group of the highest hierarchy on the magnetic tape T in the recording order corresponding to the order from the top to the bottom of the hierarchy for each group of the highest hierarchy generated by the process in step S12. In addition, the controller 42 performs a control of recording the hierarchy of the group generated by the process of step S12 in the recording region for recording the management information of the magnetic tape T. Further, the controller 42 also performs a control of recording a recording position of a head object of each group in the recording region for recording the management information as a recording position on the magnetic tape T of each group. In a case where the process of step S14 ends, the main recording process ends.

Figure 8:
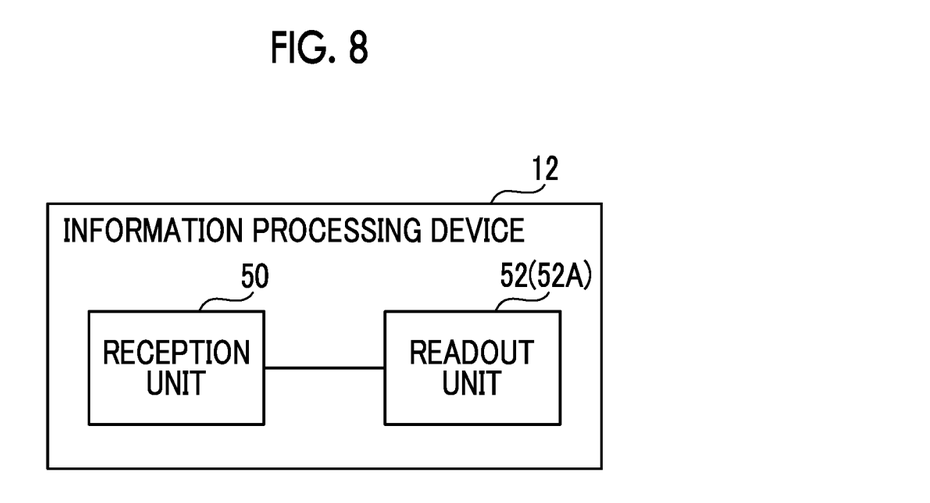
FIG. 8 is a block diagram showing an example of a functional configuration in a case of reading an object of an information processing device according to each embodiment.

Next, a functional configuration of the information processing device 12 in a case where the object is read from the magnetic tape T on which the object is recorded as described above will be described with reference to FIG. 8. As shown in FIG. 8, the information processing device 12 includes a reception unit 50 and a readout unit 52. The CPU 20 executes the readout program 32 to function as the reception unit 50 and the readout unit 52.

The reception unit 50 receives the identification information of the object to be read. In the present embodiment, the reception unit 50 receives, as the identification information of the object to be read, the identification information of the group to which the object to be read belongs, for example, such as "patient A" or "Jul. 1, 2018". It should be noted that the identification information received by the reception unit 50 may be identification information of one group such as "patient A" or identification information of a plurality of groups such as "patient A" and "Jul. 1, 2018". This identification information is input by the user as a search condition, for example.

The readout unit 52 reads an object corresponding to the identification information received by the reception unit 50 from the magnetic tape T on which a plurality of objects are recorded by the recording process shown in FIG. 7.

Specifically, the readout unit 52 reads the hierarchy of the group and the recording position of the object from the recording region for recording the management information on the magnetic tape T. In addition, the readout unit 52 specifies a recording position on the magnetic tape T corresponding to the object depending on the identification information received by the reception unit 50 by using the hierarchy of the read group and the recording position of the object. Then, the readout unit 52 reads the object corresponding to the identification information received by the reception unit 50 from the specified recording position.

As an example, a case will be described in which the objects are recorded on the magnetic tape T in the recording order shown in FIG. 6 and the user wants to refer to the "patient A" objects. In this case, "patient A" is designated as the object identification information by the user, and is received by the reception unit 50.

In this case, the readout unit 52 can continuously read all the objects included in the "patient A" from the head object of the "patient A" in one reading operation. Therefore, by arranging the hierarchy of groups in an order in which it is most likely to be read from the top, more objects can be read at once, and as a result, the reading time of the object recorded on the magnetic tape T can be shortened.

Figure 9:
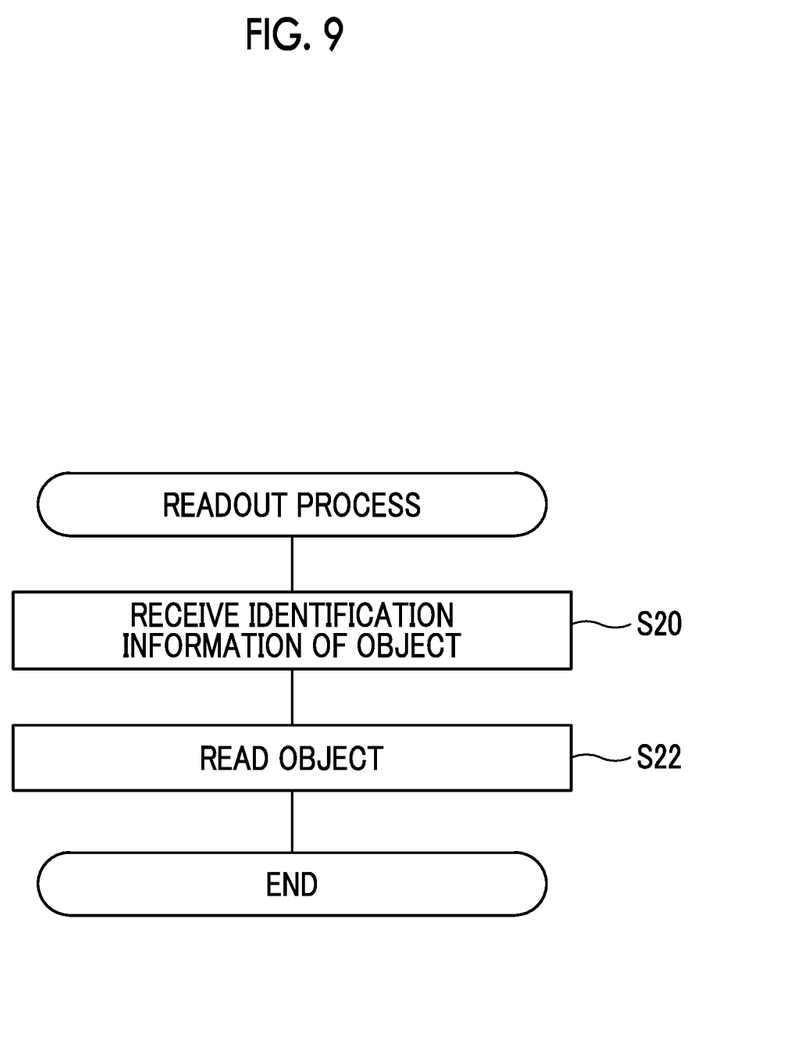
FIG. 9 is a flowchart showing an example of a readout process according to the first embodiment.

Next, an operation in a case where the object is read from the magnetic tape T of the information processing device 12 according to the present embodiment will be described with reference to FIG. 9. In a case where the CPU 20 executes the readout program 32, the readout process shown in FIG. 9 is executed. The readout process shown in FIG. 9 is executed, for example, in a case where the identification information of the object to be read is input by the user via the input unit 24.

In step S20 of FIG. 9, the reception unit 50 receives the identification information of the object to be read, as described above.

In step S22, as described above, the readout unit 52 reads the hierarchy of the group and the recording position of the object from the recording region for recording the management information on the magnetic tape T. In addition, the readout unit 52 specifies a recording position on the magnetic tape T corresponding to the object depending on the identification information received by the process of step S20 by using the hierarchy of the read group and the recording position of the object. Then, the readout unit 52 reads the object corresponding to the identification information received by the process of step S20 from the specified recording position. In a case where the process of step S22 ends, the main recording process ends.

Second Embodiment

A second embodiment of the disclosed technology will be described. In the present embodiment, an aspect example in which the same data is recorded on each of the plurality of magnetic tapes T will be described. It should be noted that the configuration of the recording/readout system 10 (refer to FIG. 1) and the hardware configuration of the information processing device 12 (refer to FIG. 2) according to the present embodiment are the same as those in the first embodiment, and thus the description thereof will be omitted.

Next, a functional configuration in a case where an object is recorded on the magnetic tape T of the information processing device 12 according to the present embodiment will be described with reference to FIG. 3. It should be noted that function units having the same functions as those of the information processing device 12 according to the first embodiment are denoted by the same reference signs and will not be described. As shown in FIG. 3, the information processing device 12 includes a reception unit 40A, a generation unit 41A, and a controller 42A. By executing the recording program 30, the CPU 20 functions as the reception unit 40A, the generation unit 41A, and the controller 42A.

The reception unit 40A has the following functions in addition to the functions of the reception unit 40 according to the first embodiment. The reception unit 40A receives the number of magnetic tapes T for recording a plurality of objects to be recorded, which are input by the user via the input unit 24. It should be noted that the number of the magnetic tapes T may be stored in advance in the storage unit 22 as a set value.

The generation unit 41A has the following functions in addition to the functions of the generation unit 41 according to the first embodiment. In a case where the number of magnetic tapes T received by the generation unit 41A is 1, the reception unit 40A generates a hierarchy of groups in the same manner as the generation unit 41 according to the first embodiment.

On the other hand, in a case where the number of magnetic tapes T received by the reception unit 40A is 2 or more (that is, in a case where a plurality of objects are recorded on each of a plurality of magnetic tapes T), the generation unit 41A generates a plurality of the hierarchies by making the hierarchical orders of the hierarchies different from each other according to each of the number of magnetic tapes T received by the reception unit 40A.

Figure 10:
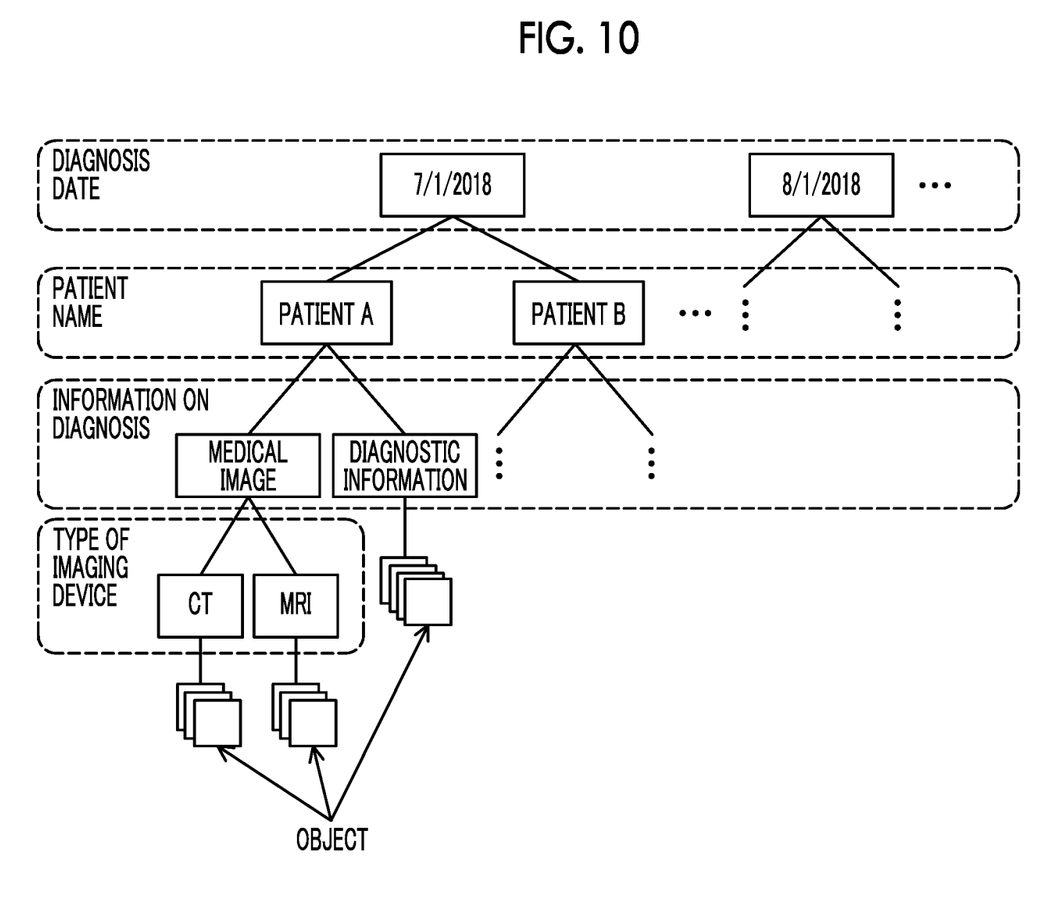
FIG. 10 is a diagram showing an example of hierarchies of groups according to the second embodiment.

As an example, a case where the reception unit 40A receives the information representing the hierarchical orders of the hierarchy shown in FIG. 4 and "2" is received as the number of magnetic tapes T will be described. In this case, the generation unit 41A generates, for example, the hierarchy shown in FIG. 5 similar to the first embodiment as the hierarchy of the first group. Further, in this case, the generation unit 41A generates a hierarchy having a different hierarchical orders from the generated hierarchy of the first group as the hierarchy of the second group. An example of the hierarchy of the second group is shown in FIG. 10. In the example shown in FIG. 10, the hierarchical orders of the hierarchy between a patient name group and a diagnosis date group in the example shown in FIG. 5 are interchanged.

The controller 42A has the following functions in addition to the functions of the controller 42 according to the first embodiment. In a case where the number of magnetic tapes T received by the reception unit 40A is 1, the controller 42A performs the same control as the controller 42 according to the first embodiment.

On the other hand, in a case where the number of magnetic tapes T received by the reception unit 40A is 2 or more, the controller 42A performs a control of recording a plurality of objects on each of the plurality of magnetic tapes in the same recording order as in the first embodiment according to each of the hierarchies generated by the generation unit 41A.

Figure 11:
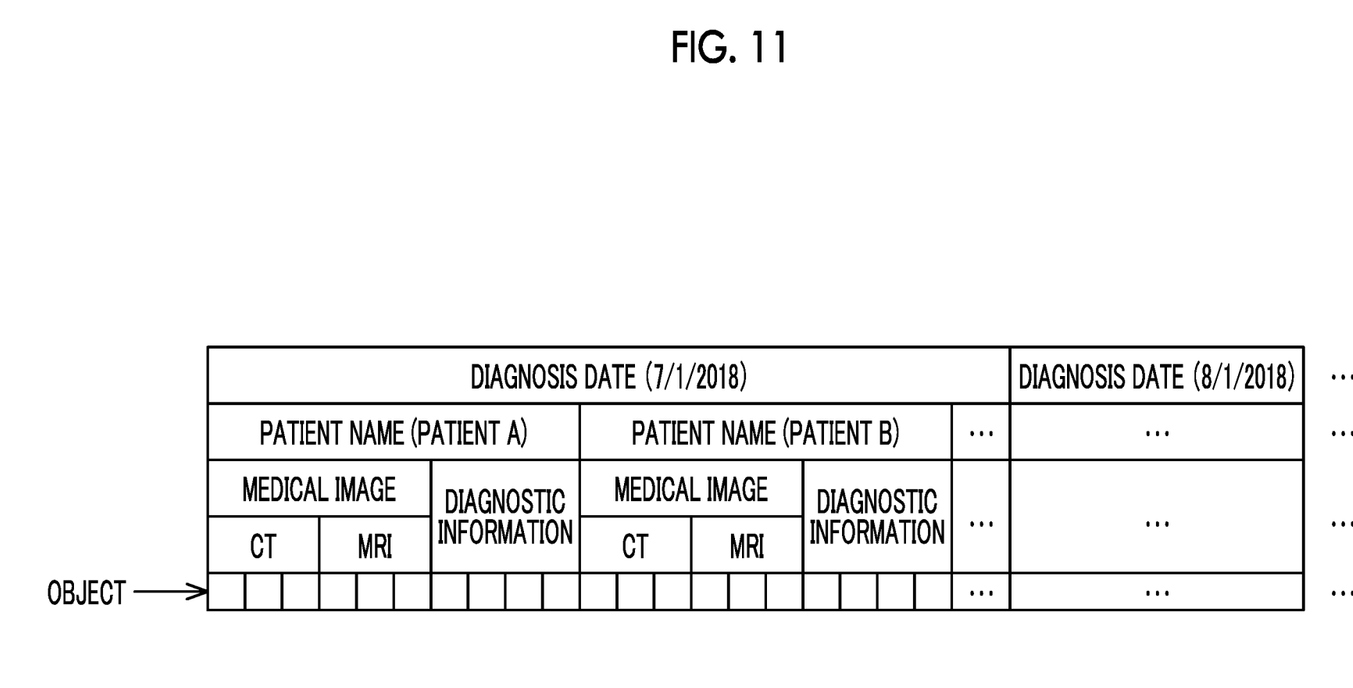
FIG. 11 is a diagram showing an example of a recording order of objects according to the second embodiment.

For example, in a case where the generation unit 41A generates the hierarchy shown in FIG. 5 and the hierarchy shown in FIG. 10, the controller 42A performs, according to the hierarchy shown in FIG. 5, a control of recording a plurality of objects on the first magnetic tape T by one recording instruction in the recording order shown in FIG. 6. Further, in this case, the controller 42A performs a control of recording a plurality of objects on the second magnetic tape T with one recording instruction in the recording order shown in FIG. 11 according to the hierarchy shown in FIG. 10. In the example shown in FIG. 11 in the same manner as the example shown in FIG. 6, the objects are recorded on the magnetic tape T in an order from the left side to the right side in FIG. 11.

Figure 12:
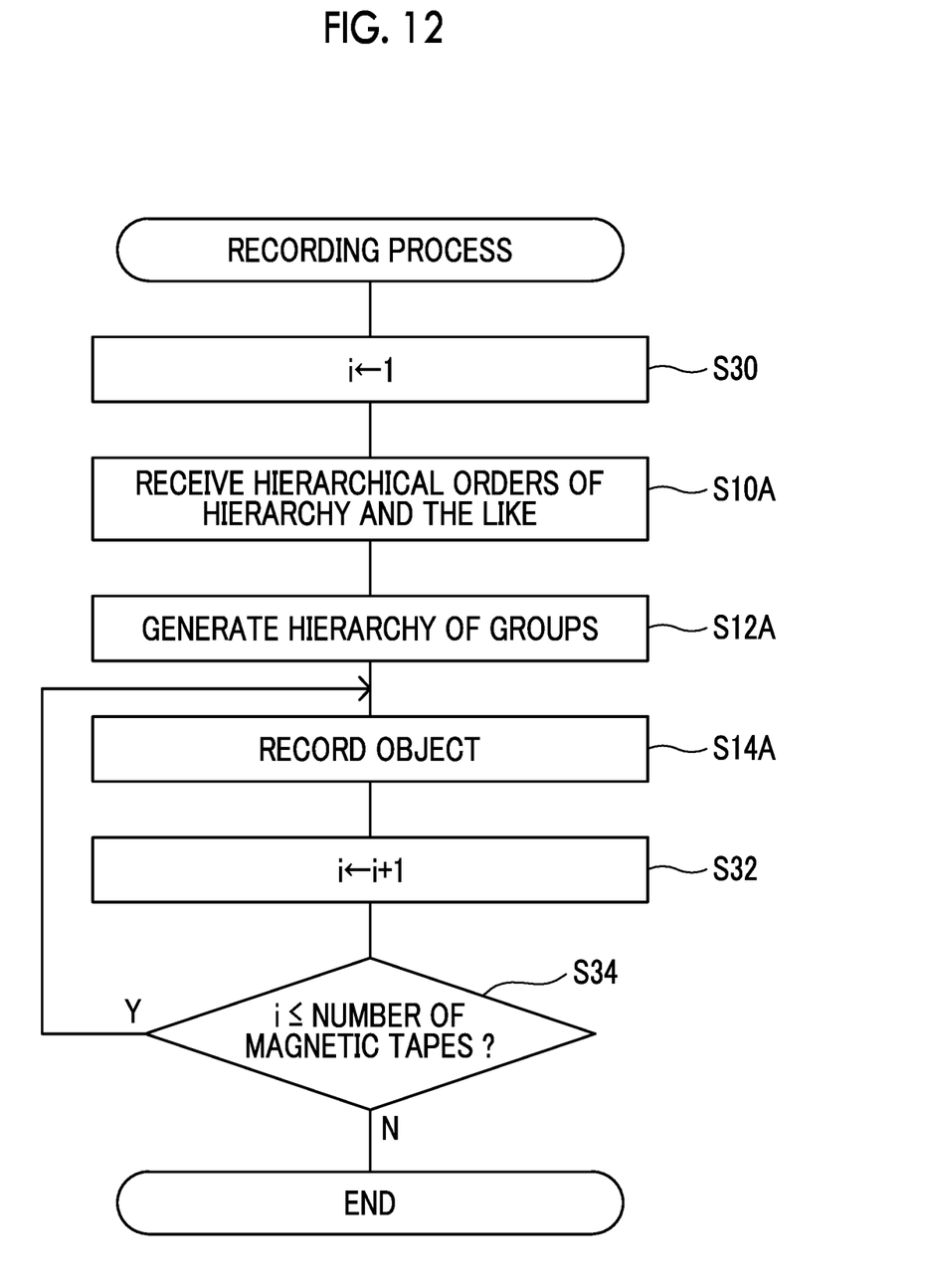
FIG. 12 is a flowchart showing an example of a recording process according to the second embodiment.

Next, an operation in a case where an object is recorded on the magnetic tape T of the information processing device 12 according to the present embodiment will be described with reference to FIG. 12. In a case where the CPU 20 executes the recording program 30, the recording process shown in FIG. 12 is executed. The recording process shown in FIG. 12 is executed, for example, in a case where the information and the number of the magnetic tapes T representing the hierarchical orders of the hierarchy described above are input by a user via the input unit 24, and the recording instruction of the object is input.

In step S30 of FIG. 12, the controller 42A substitutes 1 for a variable i for a counter. In step S10A, the reception unit 40A receives information representing the hierarchical orders of the hierarchy of the unit of the group for classifying each object and the number of magnetic tapes T.

In step S12A, as described above, the generation unit 41A generates a hierarchy of groups for classifying each object from the metadata of each of the plurality of objects to be recorded according to the information representing the hierarchical orders received by the process in step S10A. At this time, as described above, the generation unit 41A generates a hierarchy of groups of the number of magnetic tapes T received by the process of step S10A.

In step S14A, the controller 42A performs a control of recording the object on the magnetic tape T by performing the same process as in step S14 of the first embodiment. At the time of this control, the controller 42A uses the i-th hierarchy and the i-th magnetic tape T generated by the process of step S12A.

In step S32, the controller 42A adds 1 to the variable i. In step S34, the controller 42A determines whether or not the value of the variable i is equal to or less than the number of magnetic tapes T received by the process of step S10A. In a case where the determination is positive, the process returns to step S14A, and in a case where the determination is negative, the recording process ends. It should be noted that the process of recording a plurality of objects on a plurality of magnetic tapes T may be performed in parallel using a plurality of tape drives 18.

Next, a functional configuration of the information processing device 12 in a case where the object is read from the magnetic tape T on which the object is recorded as described above will be described with reference to FIG. 8. It should be noted that function units having the same functions as those of the information processing device 12 according to the first embodiment are denoted by the same reference signs and will not be described. As shown in FIG. 8, the information processing device 12 includes a reception unit 50 and a readout unit 52A. The CPU 20 executes the readout program 32 to function as the reception unit 50 and the readout unit 52A.

The readout unit 52A has the following functions in addition to the functions of the readout unit 52 according to the first embodiment. In a case where there is one magnetic tape T on which the same plurality of objects are recorded, the readout unit 52A reads an object corresponding to the identification information received by the reception unit 50 in the same manner as the readout unit 52 according to the first embodiment.

In a case where there are a plurality of magnetic tapes T on which the same plurality of objects are recorded, the readout unit 52A reads the object from the magnetic tape T on which the object to be read is recorded in the highest hierarchy among the plurality of magnetic tapes T. Specifically, the readout unit 52A reads the hierarchy of the group from the recording region for recording the management information in each magnetic tape T. Then, the group corresponding to the identification information received by the reception unit 50 specifies a magnetic tape T of the highest hierarchy, and reads an object from the specified magnetic tape T in the same manner as the readout unit 52 according to the first embodiment.

As a detailed example, a case will be described in which there are two magnetic tapes T, a magnetic tape T on which an object is recorded according to the hierarchy shown in FIG. 5 and a magnetic tape T on which an object is recorded according to the hierarchy shown in FIG. 10, and a user wants to refer to an object of "patient A".

In this case, "patient A" is designated as the object identification information by the user, and is received by the reception unit 50. In the hierarchy shown in FIG. 5, "patient A" is the highest hierarchy, and in the hierarchy shown in FIG. 10, "patient A" is the second hierarchy from the top. Therefore, in this case, the readout unit 52A reads all the objects included in the "patient A" from the magnetic tape T on which the objects are recorded according to the hierarchy shown in FIG. 5 in which the "patient A" is recorded in the highest hierarchy of the two magnetic tapes T.

On the other hand, in a case where "Jul. 1, 2018" is designated as the object identification information by the user, the readout unit 52A reads the object from the magnetic tape T shown below. That is, in this case, the readout unit 52A reads all the objects included in the "Jul. 1, 2018" from the magnetic tape T on which the objects are recorded according to the hierarchy shown in FIG. 10 in which the "Jul. 1, 2018" is recorded in the highest hierarchy of the two magnetic tapes T. Therefore, the object to be read can be read from the magnetic tape T in the most grouped state, and as a result, the reading time of the object recorded on the magnetic tape T can be shortened.

For example, in a case where identification information of the same hierarchy is designated between a plurality of magnetic tapes such as "medical image" and "diagnostic information" or "CT" and "MRI", it is not limited from which magnetic tape T the object is read. For example, the magnetic tape T to be read may be randomly determined, or the object may be read from a magnetic tape T having the smallest number of readout in the past.

Figure 13:
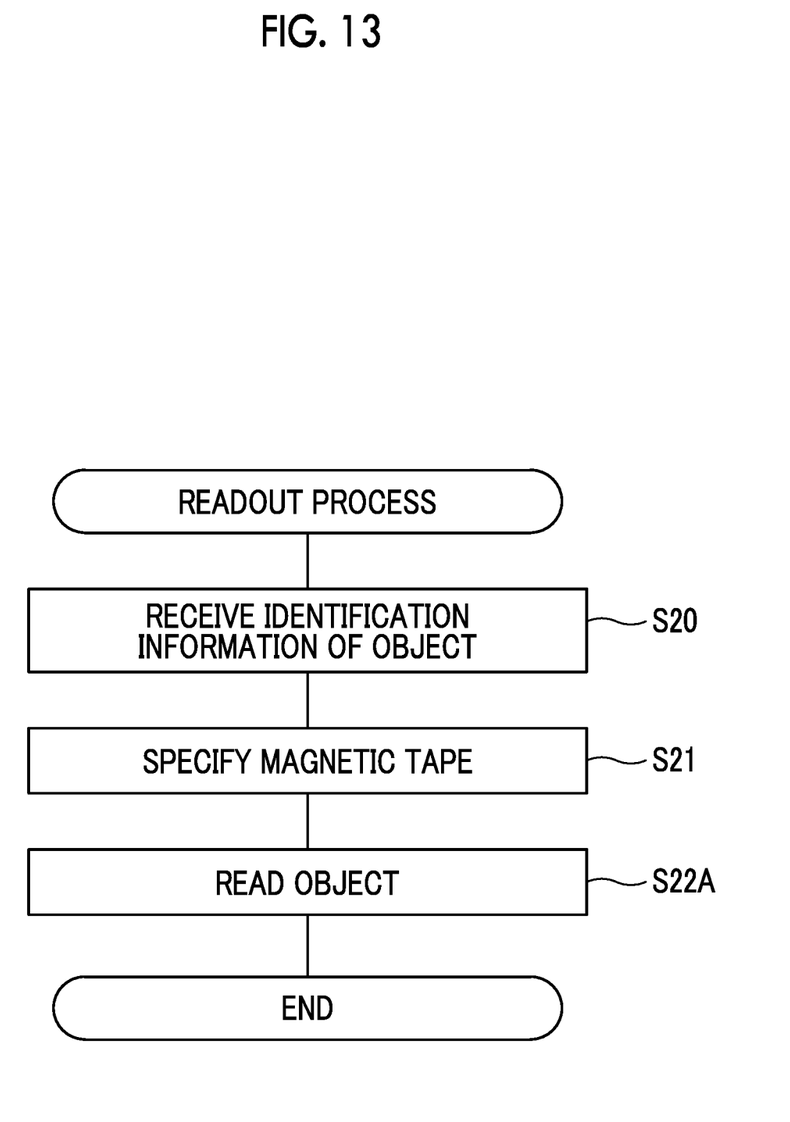
FIG. 13 is a flowchart showing an example of a readout process according to the second embodiment.

Next, an operation in a case where the object is read from the magnetic tape T of the information processing device 12 according to the present embodiment will be described with reference to FIG. 13. In a case where the CPU 20 executes the readout program 32, the readout process shown in FIG. 13 is executed. The readout process shown in FIG. 13 is executed, for example, in a case where the identification information of the object to be read is input by the user via the input unit 24. It should be noted that in the case where the object to be read is stored on one magnetic tape T, the process is the same as the readout process according to the first embodiment, and therefore, the case where the object to be read is stored on each of the plurality of magnetic tapes T will be described. In addition, the steps of performing the same process as in FIG. 9 in FIG. 13 are designated by the same reference signs and the description thereof will be omitted.

In step S21 of FIG. 13, the readout unit 52A specifies the magnetic tape T of the highest hierarchy in the group corresponding to the identification information received in the process of step S20 as described above.

In step S22A, the readout unit 52A performs the same process as in step S22 according to the first embodiment to read an object corresponding to the identification information received by the process of step S20 from the magnetic tape T specified by the process of step S21. In a case where the process of step S22A ends, the main recording process ends.

It should be noted that in each of the above-described embodiments, the case where the magnetic tape is applied as a recording medium has been described, but the present invention is not limited to this. A recording medium other than the magnetic tape may be applied as a recording medium.

In addition, in the second embodiment, a case where a plurality of objects to be recorded are recorded on each of the plurality of magnetic tapes T by one recording process has been described, but the present invention is not limited to this. For example, a plurality of objects to be recorded may be recorded on each of the plurality of magnetic tapes T by copying an object recorded on the magnetic tape T on which the object has already been recorded to another magnetic tape T. In this case, in the same manner as the second embodiment, in a hierarchy different from a hierarchy of a group recorded on the magnetic tape T on which the object has already been recorded, an aspect in which the recorded object is recorded (replicated) on another magnetic tape T is exemplified.

In addition, in each of the above-described embodiments, the case where the user inputs the hierarchical orders of the hierarchy of the group has been described, but the present invention is not limited to this. For example, the larger the number of groups included in the metadata of a plurality of objects to be recorded, the higher the hierarchy may be. Further, for example, groups with higher readout frequencies in the past may be the higher hierarchy.

In each of the above-described embodiments, a case where the disclosed technology is applied to an object storage system has been described, but the present invention is not limited to this. For example, the disclosed technology may be applied to a storage system having a hierarchical structure such as a directory.

In each of the above-described embodiments, medical data is used as data to be recorded on the magnetic tape T, but the present invention is not limited to this. For example, as the data to be recorded on the magnetic tape T, data for purposes other than medical use may be applied.

In each of the above-described embodiments, for example, the following various processors can be used as a hardware structure of a processing unit that executes various process such as the reception units 40 and 40A, the generation units 41 and 41A, the controllers 42 and 42A, the reception unit 50, and the readout units 52 and 52A. The various processors include, for example, a programmable logic device (PLD), such as FPGA, that is a processor whose circuit configuration can be changed after manufacture and a dedicated electric circuit, such as an application specific integrated circuit (ASIC), that is a processor having a dedicated circuit configuration designed to execute a specific process, in addition to the CPU that is a general-purpose processor which executes software (program) to function as various processing units as described above.

One processing unit may be configured by one of the various processors or a combination of the same or different types of two or more processors (for example, a combination of a plurality of FPGAs or a combination of a CPU and an FPGA). In addition, the plurality of processing units may be configured by one processor.

As an example where a plurality of processing units are configured by one processor, first, there is an aspect where one processor is configured by a combination of one or more CPUs and software as typified by a computer, such as a client or a server, and this processor functions as a plurality of processing units. Next, there is a second example in which a processor that implements the function of the entire system including the plurality of processing units by one integrated circuit (IC) chip is used, as represented by a system on chip (SoC) or the like. As such, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, an aspect in which the recording program 30 and the readout program 32 are stored (installed) in the storage unit 22 in advance has been described, but the present invention is not limited to this. The recording program 30 and the readout program 32 may be provided in an aspect recorded on a recording medium, such as CD-ROM, a digital versatile disc read only memory (DVD-ROM), or a universal serial bus (USB) memory. In addition, the recording program 30 and the readout program 32 may be downloaded from an external device via a network.

The present application claims the priority of JP2018-180774 filed on Sep. 26, 2018, and the entire text thereof is incorporated herein by reference.

An object of the present disclosure is to provide a recording device, a readout device, a recording method, a recording medium, a readout method, and a magnetic tape capable of shortening the reading time of data recorded on a recording medium.

A recording device of the present disclosure includes: a memory, and a processor that is coupled to the processor, the processor being configured to: generate a hierarchy of groups for classifying each of a plurality of data to be recorded from information on each of the data, and perform a control of recording, for each group of the highest hierarchy, the plurality of data included in the group of the highest hierarchy on a recording medium in a recording order corresponding to an order from the top to the bottom of the hierarchy.

It should be noted that in the recording device of the present disclosure, the processor may be configured to perform a control of recording the plurality of data on the recording medium by one recording instruction.

In the recording device of the present disclosure in a case where the plurality of data are recorded on each of a plurality of the recording mediums, the processor may be configured to: generate a plurality of the hierarchies by making hierarchical orders of the hierarchies different from each other according to each of the plurality of recording mediums, and perform a control of recording the plurality of data on each of the plurality of recording mediums in the recording order depending on each of the hierarchies.

In the recording device of the present disclosure, the processor may be configured to receive information representing the hierarchical orders of the hierarchy.

In the recording device according to the present disclosure, the recording medium may be a magnetic tape.

A readout device of the present disclosure includes: a memory; and a processor that is coupled to the memory, the processor being configured to: receive identification information of data to be read, and read the data corresponding to the identification information from a recording medium on which a plurality of data included in groups of the highest hierarchy are recorded in a recording order corresponding to an order from the top to the bottom of the hierarchy for each group of the highest hierarchy in the hierarchies of groups for classifying each of the plurality of data, which are generated from information on each of the data.

In the readout device of the present disclosure, in a case where the data to be read is read from a plurality of recording mediums on which the plurality of data are recorded in the recording order depending on a plurality of the hierarchies having different hierarchical orders, the processor may be configured to read the data from the recording medium on which the data to be read is recorded in the highest hierarchy among the plurality of recording mediums.

A recording method of the present disclosure includes: by a processor, generating a hierarchy of groups for classifying each of a plurality of data to be recorded from information on each of the data, and performing a control of recording, for each group of the highest hierarchy, the plurality of data included in the group of the highest hierarchy on a recording medium in a recording order corresponding to an order from the top to the bottom of the hierarchy.

A non-transitory computer-readable recording medium that records a program that is executable by a computer to perform a process, the process including generating a hierarchy of groups for classifying each of a plurality of data to be recorded from information on each of the data, and performing a control of recording, for each group of the highest hierarchy, the plurality of data included in the group of the highest hierarchy on a recording medium in a recording order corresponding to an order from the top to the bottom of the hierarchy.

A readout method of the present disclosure includes: by a processor, receiving identification information of data to be read, and reading the data corresponding to the identification information from a recording medium on which a plurality of data included in groups of the highest hierarchy are recorded in a recording order corresponding to an order from the top to the bottom of the hierarchy for each group of the highest hierarchy in the hierarchies of groups for classifying each of the plurality of data, which are generated from information on each of the data.

A non-transitory computer-readable recording medium that records a program that is executable by a computer to perform a process, the process including receiving identification information of data to be read, and reading the data corresponding to the identification information from a recording medium on which a plurality of data included in groups of the highest hierarchy are recorded in a recording order corresponding to an order from the top to the bottom of the hierarchy for each group of the highest hierarchy in the hierarchies of groups for classifying each of the plurality of data, which are generated from information on each of the data.

A magnetic tape of the present disclosure is a magnetic tape on which a plurality of data included in groups of the highest hierarchy are recorded in a recording order corresponding to an order from the top to the bottom of the hierarchy for each group of the highest hierarchy in the hierarchies of groups for classifying each of the plurality of data, which are generated from information on each of the data.

According to the present disclosure, it is possible to shorten the reading time of the data recorded on the recording medium.

What is claimed is:

1. A recording device comprising:
a memory; and
a processor that is coupled to the memory, the processor being configured to:
generate a hierarchy of groups for classifying each of a plurality of data to be recorded from information on each of the data; and
perform a control of recording, for each group of a highest hierarchy, the plurality of data included in the group of the highest hierarchy on a recording medium in a recording order corresponding to an order from the top to the bottom of the hierarchy.

2. The recording device according to claim 1, wherein the processor is configured to perform a control of recording the plurality of data on the recording medium by one recording instruction.

3. The recording device according to claim 1, wherein in a case where the plurality of data are recorded on each of a plurality of recording mediums, the processor is configured to:
generate a plurality of hierarchies by making hierarchical orders of the plurality of hierarchies different from each other according to each of the plurality of recording mediums, and
perform a control of recording the plurality of data on each of the plurality of recording mediums in the recording order depending on each of the generated plurality of hierarchies.

4. The recording device according to claim 1, wherein the processor is configured to receive information representing hierarchical orders of the hierarchy.

5. The recording device according to claim 1, wherein the recording medium is a magnetic tape.

6. A recording method comprising:
by a processor,
generating a hierarchy of groups for classifying each of a plurality of data to be recorded from information on each of the data; and
performing a control of recording, for each group of a highest hierarchy, the plurality of data included in the group of the highest hierarchy on a recording medium in a recording order corresponding to an order from the top to the bottom of the hierarchy.

7. A non-transitory computer-readable recording medium that records a program that is executable by a computer to perform a process, the process comprising:
generating a hierarchy of groups for classifying each of a plurality of data to be recorded from information on each of the data; and
performing a control of recording, for each group of a highest hierarchy, the plurality of data included in the group of the highest hierarchy on a recording medium in a recording order corresponding to an order from the top to the bottom of the hierarchy.

* * * * *

UNITED STATES PATENT AND TRADEMARK OFFICE
CERTIFICATE OF CORRECTION

| | | |
|---|---|---|
| PATENT NO. | : 11,915,726 B2 | Page 1 of 1 |
| APPLICATION NO. | : 17/210507 | |
| DATED | : February 27, 2024 | |
| INVENTOR(S) | : Kentaro Miyamoto | |

It is certified that error appears in the above-identified patent and that said Letters Patent is hereby corrected as shown below:

On the Title Page

Item (54), and in the Specification, Column 1 Line 1 the Title should be corrected to read: RECORDING DEVICE, READOUT DEVICE, RECORDING METHOD, RECORDING PROGRAM, READOUT METHOD, READOUT PROGRAM, AND MAGNETIC TAPE CAPABLE OF SHORTENING THE READING TIME OF DATA RECORDED ON A RECORDING MEDIUM Signed and Sealed this
Second Day of July, 2024

Katherine Kelly Vidal
*Director of the United States Patent and Trademark Office*